United States Patent [19]

Rothgery

[11] Patent Number: 5,009,700

[45] Date of Patent: Apr. 23, 1991

[54] USE OF PYRITHIONE FOR THE CONTROL OF MOSS

[75] Inventor: Eugene F. Rothgery, North Branford, Conn.

[73] Assignee: Olin Corporation, Cheshire, Conn.

[21] Appl. No.: 558,279

[22] Filed: Jul. 26, 1990

[51] Int. Cl.$^5$ .................. A01N 43/40; A01N 55/02; A01N 31/08

[52] U.S. Cl. .......................................... 71/94; 71/97; 71/98

[58] Field of Search ............................ 71/94, 65, 97

[56] References Cited

U.S. PATENT DOCUMENTS

| | | | |
|---|---|---|---|
| 2,809,971 | 10/1957 | Bernstein et al. | 260/270 |
| 3,107,994 | 10/1963 | Rawlings et al. | 71/2.5 |
| 3,159,640 | 12/1964 | McClure et al. | 260/294.8 |
| 4,039,312 | 8/1977 | Patru | 71/67 |
| 4,818,436 | 4/1989 | French et al. | 252/400 |
| 4,935,061 | 6/1990 | French et al. | 106/170 |

Primary Examiner—Allen J. Robinson
Assistant Examiner—Brian M. Burn
Attorney, Agent, or Firm—Dale Lynn Carlson

[57] ABSTRACT

The present invention relates to a process for ridding moss from an unwanted location such as lawns, walls, monuments, building foundations, tombstones, and combinations thereof which comprises contacting moss growing in said unwanted location with a mossicidal effective amount of a pyrithione salt.

5 Claims, No Drawings

USE OF PYRITHIONE FOR THE CONTROL OF MOSS

FIELD OF THE INVENTION

This invention relates to a new use of pyrithiones, and, more specifically, to a process for controlling moss by treating the moss with an effective amount of a pyrithione compound.

BACKGROUND OF THE INVENTION

The use of zinc pyrithione and sodium pyrithione as a bacteriacide/fungicide in paints, metalworking fluids, wood preservatives and personal care items such as shampoos is well-known in the art. By way of illustration. U.S. Pat. No. 4,818,436 discloses the use of pyrithiones in metalworking fluids, and U.S. Pat. No. 4,935,061 discloses their use in paints.

In the past, the use of sodium and zinc pyrithiones in agricultural products, such as crop treatments, has been impeded due to the relative instability of sodium pyrithione and zinc pyrithione in the presence of ultraviolet (uv) light. In the presence of uv light, such as sunlight, the pyrithione molecule degrades causing a loss of biocidal efficacy.

Heretofore, typical methodology for the eradication of moss from grass growing in a lawn has been to rake out the moss, fertilize the ground and re-seed with grass. This raking treatment is hard on the grasses growing in the area. Accordingly, it would be desirable to provide a simpler moss treatment method that selectively eradicates moss in a lawn without harming the grass in the lawn. Heretofore, such a treatment method was not known to the knowledge of the present inventor.

SUMMARY OF THE INVENTION

In one aspect, the present invention relates to a process for ridding moss from an unwanted location which comprises contacting the moss with a mossicidal effective amount of sodium pyrithione, zinc pyrithione, or a combination thereof.

This and other aspects will become apparent from a reading of the following detailed description of the invention.

DETAILED DESCRIPTION OF THE INVENTION

The sodium pyrithione employed in the process of the present invention is a well-known commercial product and is commonly made by reacting 2-chloropyridine-N-oxide with NaSH and NaOH, as disclosed in U.S. Pat. No. 3,159,640.

Zinc pyrithione may be made by reacting 1-hydroxy-2-pyridinethione or a soluble salt thereof with a zinc salt (e.g., $ZnSO_4$) to form a zinc pyrithione precipitate, as disclosed in U.S. Pat. No. 2,809,971.

In the process of the present invention, the zinc pyrithione, sodium pyrithione, or combination thereof, is employed in a "mossicidal effective amount" which designates an amount of the selected pyrithione salt sufficient to eradicate any living moss in an undesirable location without harming grass growing on the lawn. Preferably, this amount is between about 5 and about 100 milligrams/sq. ft. of the moss to be eradicated.

Although the preferred pyrithione salts useful in the process of the present invention are sodium pyrithione, zinc pyrithione, or a combination thereof, other pyrithione salts are also suitably employed within the scope of the present invention, including, for example, copper, aluminum and magnesium.

Moss grows in many undesirable location such as, for example, on lawns together with grass, or growing on structures such as walls, monuments, building foundations, tombstones, and the like. Moss growing on such structures causes cosmetic (e.g., discoloration) problems and surface damage problems to the structures. The process of the present invention is suitable for eradicating moss growing in any of these undesirable locations.

When the process of the present invention is used to treat moss growing on lawns, it has now been surprisingly found that the moss is effectively eradicated without any damage to the grass growing on the lawn in the vicinity of the treated moss.

The mossicidal composition useful in the process of the present invention suitably contains, in addition to the pyrithione salt, optional additives such as surfactants (such as polyalkoxylated surfactants commercially available as POLYTERGENT® B300), wetting agents, stabilizers, and the like, and combinations thereof.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated herein by reference in their entirety.

EXAMPLE 1

Testing of Sodium Pyrithione Solution on Moss Growing in Grass on a Lawn

An aqueous solution of sodium pyrithione having a 40% twenty five milliliter of active ingredient and commercially available as sodium OMADINE, a product of Olin Corporation, was added to 2 gallons of water in a portable sprayer. One milliliter of surfactant Polytergent® B300 from Olin was added to aid in wetting the moss. This solution has a concentration of pyrithione salt of about 1675 ppm. It was applied to the moss in the evening because the pyrithione solutions typically are not stable in the presence of light without added UV stabilizers. (This light instability is advantageous for the present use since moss frequently grows in shady areas, and light degradation of the pyrithione salt after eradicating the moss is environmentally desirable.) The moss was sprayed enough to be thoroughly wetted. After a period of 5 days, the mosses had turned yellow to brown and had lost vitality.

EXAMPLE 2

Testing of a Dilute Aqueous Solution of Sodium Pyrithione on Moss Growing in Various Locations Fifteen grams of a 40% aqueous solution of sodium pyrithione commercially available as sodium OMADINE, a product of Olin Corporation, was mixed with one milliliter of the same surfactant in 2 gallons (7.6 liters) of water in a hand sprayer. This produced a solution containing 789 mg/liter (ppm) of active ingredient. This solution was then applied to moss growing in lawns, on tree trunks and on concrete foundations. After three days the moss began to turn from green to tan in color. After five days it had become brown and lost vitality.

What is claimed is:

1. A process for ridding moss from an unwanted location which comprises contacting the moss with a mossicidal effective amount of sodium pyrithione, zinc pyrithione, or a combination thereof.

2. The process of claim 1 wherein said amount of sodium pyrithione, zinc pyrithione, or a combination thereof, is between about 5 and about 100 milligrams per square foot of the moss to be eradicated.

3. A process for ridding moss from an unwanted location selected from the group consisting of lawns, walls, monuments, building foundations, tombstones, and combinations thereof which comprises contacting moss growing in said unwanted location with a mossicidal effective amount of a pyrithione salt.

4. The process of claim 3 wherein said pyrithione salt is selected from the group consisting of sodium pyrithione, zinc pyrithione, copper pyrithione, aluminum pyrithione, magnesium pyrithione, and combinations thereof.

5. The process of claim 3 wherein said pyrithione salt is employed in an amount of between about 5 and about 100 milligrams per square foot of the moss to be eradicated.

* * * * *